(12) United States Patent
Biel (10) Patent No.: US 8,187,278 B2
(45) Date of Patent: May 29, 2012

(54) PHOTODYNAMIC CELLULAR AND ACELLULAR ORGANISM ERADICATION UTILIZING A PHOTOSENSITIVE MATERIAL AND BENZALKONIUM CHLORIDE

(75) Inventor: Merrill A. Biel, Mendota Heights, MN (US)

(73) Assignee: Advanced Photodynamic Technologies, Inc., Minneapolis, MN (US)

( * ) Notice: Subject to any disclaimer, the term of this patent is extended or adjusted under 35 U.S.C. 154(b) by 2691 days.

(21) Appl. No.: 10/026,198

(22) Filed: Dec. 21, 2001

(65) Prior Publication Data

US 2002/0091424 A1    Jul. 11, 2002

Related U.S. Application Data

(63) Continuation-in-part of application No. 09/792,578, filed on Feb. 23, 2001, which is a continuation-in-part of application No. 09/514,070, filed on Feb. 26, 2000, which is a continuation-in-part of application No. 09/139,866, filed on Aug. 25, 1998, now Pat. No. 6,251,127.

(51) Int. Cl.
    *A61N 5/06*    (2006.01)
(52) U.S. Cl. ......................................... 606/88
(58) Field of Classification Search .................... 607/88, 607/89
    See application file for complete search history.

(56) References Cited

U.S. PATENT DOCUMENTS

| | | | |
|---|---|---|---|
| 4,879,135 A | | 11/1989 | Greco et al. |
| 5,240,675 A | * | 8/1993 | Wilk et al. ................. 606/15 |
| 5,260,020 A | * | 11/1993 | Wilk et al. ................. 606/15 |
| 5,262,401 A | * | 11/1993 | Vogel et al. ................. 514/32 |
| 5,707,366 A | | 1/1998 | Solomon et al. |
| 5,707,739 A | * | 1/1998 | Wellinghoff et al. ......... 428/403 |
| 5,853,745 A | | 12/1998 | Darouiche |

OTHER PUBLICATIONS

"Polycations Sensitize Enteric Bacteria to Antibiotics" Vaara et al; Antimicrobial Agents & Chemotherapy; Jul. 1983; 107-113.*
Nitzan et al; "Inactivation of Gram-Negative Bacteria by Photosensitized Porphyrins"; Photocem. & Photobiol; vol. 55, No. 1; pp. 89-96; 1992.*
New Approaches for Prevention of Intravascular Catheter-Related Infections. Hend Hanna, MD, MPH; Issam Raad, MD, The University of Texas M.D. Anderson Cancer Center, Houston; Rabih Darouiche, MD, Baylor College of Medicine, Houston [Infect Med 18(1):38-48, 2001.

(Continued)

*Primary Examiner* — David Shay
(74) *Attorney, Agent, or Firm* — Dobrusin & Thennisch PC (57) ABSTRACT

The invention relates to a method of photoeradication of cellular and acellular organisms including the steps of providing a surface acting agent containing benzalkonium chloride in association with a cellular or acellular organism, the surface acting agent disorienting a membrane structure so that said membrane no longer functions as an effective osmotic barrier; providing a photosensitive material in association with the cellular or acellular organism; and applying light in association with the cellular or acellular organism to cause a disruption of the organism. The method according to the present invention may be utilized in invitro and invivo treatment protocols for infections, sterilization procedures, cancer cell eradication, virus and fungus eradication, spore eradication, and biofilm organism eradication. Additional aspects of the invention include particular combinations of photosensitive materials and surfactants for use in photodynamic therapies.

44 Claims, 6 Drawing Sheets

OTHER PUBLICATIONS

Material Safety Data Sheet, 50% Benzalkonium Chloride. Article on Internet at www.syndel.com/msds/bkc50_msds.html (Nov. 12, 2001).

Safety Data for Benzalkonium Chloride. Article on Internet at www.physchem.ox.ac.uk/MSDS/BE/benzalkoniumchloride.html (Nov. 12, 2001).

"Benzalkonium Chloride is Unacceptable to Sterilize or Disinfect Medical or Dental Instruments," Enrique Acosta-Gio, CD, PhD, Salud Publica de Mexico, vol. 43, No. 6, Nov.-Dec. 2001.

"Zephiran" (benzalkonium chloride), www.sanofi-synthelabous.com.

* cited by examiner

FIG. 1

Photokilling of different microorganisms using methylene blue-benzalkonium mediated photodynamic therapy.

| Organism | Methylene Blue (μg/mL) | Benzalkonium (%) | Power[a] (W) | Dose Rate (mW/cm²) | Light Dose (J/cm²) | Treatment No Light | Treatment Light |
|---|---|---|---|---|---|---|---|
| C. albicans (patient iso.) | 0 | 0.0075 | N/a[b] | N/a | N/a | 3[c] | N/a |
|  | 100 | 0 | 113 | 100 | 40 | N/a | 2 |
|  | 100 | 0.005 | " | " | " | N/a | 0 |
| C. albicans 14053 | 0 | 0.0075 | N/a | N/a | N/a | 2 (19) | N/a |
|  | 100 | 0 | 113 | 100 | 30 | N/a | 1 (3) |
|  | 100 | 0.005 | " | " | " | N/a | 0 |
| E. coli 35218 | 0 | 0.0075 | N/a | N/a | N/a | 2 | N/a |
|  | 50 | 0 | 113 | 100 | 30 | N/a | 2 |
|  | 50 | 0.005 | " | " | " | N/a | 1 |
|  | 50 | 0.0075 | " | " | " | N/a | 0 |
| E. faecalis 51229 | 0 | 0.0075 | N/a | N/a | N/a | 2 (13) | N/a |
|  | 50 | 0 | 113 | 100 | 30 | N/a | 0 |
|  | 50 | 0.005 | " | " | " | N/a | 0 |
| H. influenzae (patient iso.) | 0 | 0.005 | N/a | N/a | N/a | 2 | N/a |
|  | 50 | 0 | 113 | 100 | 30 | N/a | 0 |
|  | 50 | 0.005 | " | " | " | N/a | 0 |
| K. pneumoniae 13882 | 0 | 0.0075 | N/a | N/a | N/a | 2 | N/a |
|  | 50 | 0 | 113 | 100 | 30 | N/a | 0 |
|  | 50 | 0.005 | " | " | " | N/a | 0 |
| P. aeruginosa 27853 | 0 | 0.01 | N/a | N/a | N/a | 2 | N/a |
|  | 100 | 0 | 113 | 100 | 40 | N/a | 4 |
|  | 100 | 0.01 | " | " | " | N/a | 0 |
| S. marcescens (patient iso.) | 0 | 0.0075 | N/a | N/a | N/a | 0 | N/a |
|  | 50 | 0 | 113 | 100 | 30 | N/a | 0 |
|  | 50 | 0.005 | " | " | " | N/a | 0 |
| S. aureus 29213 | 0 | 0.0075 | N/a | N/a | N/a | 1 (4) | N/a |
|  | 50 | 0 | 113 | 100 | 30 | N/a | 1 |
|  | 50 | 0.005 | " | " | " | N/a | 0 |
| S. pneumoniae 49619 | 0 | 0.005 | N/a | N/a | N/a | 0 | N/a |
|  | 50 | 0 | 113 | 100 | 30 | N/a | 0 |
|  | 50 | 0.005 | " | " | " | N/a | 0 |

[a]Wavelength = 664 nm.
[b]N/a = Not applicable.
[c]Qualitative score: 0 = no growth, 1 = 1-5, 2 = 6-100, 3 = 101-300, 4 = 301+, ( ) = number of colonies.

*FIG. 2*

Photokilling of bacterial spores using methylene green-benzalkonium chloride mediated photodynamic therapy.

| Organism | Methylene Green (μg/mL) | Benzalkonium (%) | Power[a] (W) | Dose Rate (mW/cm$^2$) | Light Dose (J/cm$^2$) | Treatment | |
|---|---|---|---|---|---|---|---|
| | | | | | | No Light | Light |
| *Bacillus subtilis* 19659 | 0 | 0 | N/a[b] | N/a | N/a | 4[c] | N/a |
| | 0 | 0.3 | N/a | N/a | N/a | 1 (2) | N/a |
| | 0 | 0.5 | N/a | N/a | N/a | 1 | N/a |
| | 150 | 0 | 170 | 150 | 60 | N/a | 4 |
| | 150 | 0.3 | " | " | " | N/a | 2 (15) |
| | 150 | 0.5 | " | " | " | N/a | 1 |
| | 200 | 0 | " | " | " | N/a | 4 |
| | 200 | 0.3 | " | " | " | N/a | 2 (8) |
| | 200 | 0.5 | " | " | " | N/a | 1 |
| | 250 | 0 | " | " | " | N/a | 4 |
| | 250 | 0.3 | " | " | " | N/a | 0 |
| | 250 | 0.5 | " | " | " | N/a | 0 |

[a]Wavelength = 664 nm.
[b]N/a = Not applicable.
[c]Qualitative score: 0 = no growth, 1 = 1-5, 2 = 6-100, 3 = 101-300, 4 = 301+, ( ) = number of colonies.

*FIG. 3*

Photodynamic Therapy of Endotracheal Tubes using Methylene Blue and Benzalkonium Chloride

| Patient | Intubation (Days) | Illness | Antibiotic | MB (μg/mL) | Benz (%) | Treatment Stage[a] | | |
|---|---|---|---|---|---|---|---|---|
| | | | | | | M-L-[b] | M+L+[c] | 2L+[d] |
| MK | 4 | Pneumonia | Ceftriaxone | 200 | 0.01 | 4[e] | 0 | 0 |
| MS | 11 | Pneumonia | Rocephin | " | " | 4 | 0 | 0 |
| MB | 1 | Surgery | N/a | " | " | 0 | 0 | 0 |
| NV | 3 | Pneumonia | Ampicillin | " | " | 2 | 0 | 0 |
| JF | 3 | Pneumonia | Primaxim | " | " | 2 | 0 | 0 |
| SR | 3 | Pneumonia | Tequin | " | " | 4 | 2 | 0 |
| AW | 2 | Surgery | N/a | " | 0.0075 | 4 | 3 | 2 |
| MZ | 16 | Pneumonia | Amt, Cln, Imi, Teq, Van | " | 0.0075 | 4 | 4 | 4 |

N/a = not applicable.
[a]Laser criteria: power = 800 mW, dose rate = 300 mW/cm, light dose = 70 J/cm, time = 233 sec
[b]M-L- = no methylene blue or light activation.
[c]M+L+ = methylene blue and light activation.
[d]2L+ = double light activation.
[e]Qualitative score: 0 = 0 colonies, 1 = 1-5, 2 = 6-100, 3 = 101-300, 4 = 301+

PHOTODYNAMIC CELLULAR AND ACELLULAR ORGANISM ERADICATION UTILIZING A PHOTOSENSITIVE MATERIAL AND BENZALKONIUM CHLORIDE

RELATED APPLICATIONS

This is a continuation-in-part of application No. 09/792,578 filed Feb. 23, 2001, which is a continuation-in-part of application No. 09/514,070 filed Feb. 26, 2000, which is a continuation-in-part of application No. 09/139,866, filed Aug. 25, 1998, now U.S. Pat. No. 6,251,127.

FIELD OF THE INVENTION

The invention relates to a photodynamic therapy (PDT) or process, and more particularly to a photodynamic therapy or process utilizing a photosensitive material and a chemical agent, such as a surfactant material, for in vitro and in vivo cellular and acellular organism eradication. The invention also relates to photodynamic eradication of bacteria, fungal, and viral wound infections and sterilization of tissue using a photosensitive material, such as methylene blue, methylene green, or toluidene blue, and a surfactant material, such as polymyxin B, SDS, cetrimide, or benzalkonium chloride. Additionally, the invention relates to photodynamic eradication of cancer cells, such as present within a tumor, by PDT in conjunction with a photosensitive material and a surfactant. The present invention advantageously uses light energy in combination with a photosensitive material and a surfactant material to treat both in vitro and in vivo pathogens, including cancer cells and microbiological pathogens. The invention also relates to the eradication or destruction of biofilms via a photodynamic mechanism. The invention also relates to an apparatus and method of use for eradication of biofilms on a diverse range of medical products, such as intravascular catheters, endotracheal tubes, and implants. The invention further relates to an apparatus and method of use for eradication of cellular and acellular organisms within an air filtration or air decontamination device for eliminating or reducing harmful biological elements such as viruses, bacteria, and fungus. The invention further relates to the eradication of spores in both in vivo and in vitro applications.

BACKGROUND OF THE INVENTION

Abnormal cells and acellular organisms are known to selectively absorb certain dyes (photosensitive materials) delivered to a treatment site to a more pronounced extent than surrounding tissue. Once presensitized, abnormal cells or acellular organisms can be destroyed by irradiation with light of an appropriate wavelength corresponding to an absorbing wavelength of the photosensitive material, with minimal damage to surrounding normal tissue. This procedure, which is known as photodynamic therapy (PDT), has been clinically used to treat metastatic breast cancer, bladder cancer, head and neck cancers, esophageal cancer, lung cancer, and other types of malignant tumors, actinic keritosis, and macular degeneration.

U.S. Pat. No. 5,676,959 to Heitz et al., purportedly discloses an ingestible phototoxic insecticidal composition including a photoactive dye, an attractant compound and/or feeding stimulant, and an adjuvant, whereby the adjuvant interacts with the photoactive dye and insect gastrointestinal (GI) tract to facilitate transport of the phototoxic insecticide across the GI tract. The use of an adjuvant to facilitate pharmaceutical uptake via GI tract absorption is known in the art. Unlike the surface acting agents of the Applicant's present invention, these adjuvants do not produce a disorientation of a cell membrane so that the cell membrane no longer functions as an effective osmotic barrier.

The article "Inactivation of Gram-Negative Bacteria by Photosensitized Porphyrins" by Nitzan, et al., published in Photochemistry and Photobiology, Vol. 55, No. 1, pp. 89-96, 1992, purportedly discloses the use of polycationic agent polymyxin nonapeptide (PMNP) in association with a photoactive agent, deuteroporphyin (DP). PMNP is disclosed to disturb the outer membrane of a gram-negative bacteria so as to permit access of the DP to bind to the internal lipoprotein osmotic membrane of the bacterial cell. PMNP is disclosed to only disturb the outer membrane structure and not its function, and not cause metabolic leakage from the cells (or osmotic changes in the cell). Unlike the surface acting agent of the Applicant's present invention, PNMP does not produce a disorientation of a cell membrane so that the cell membrane no longer functions as an effective osmotic barrier. In the Applicant's present invention, the surface acting agent causes a disorientation of the cell membrane thereby compromising the effective osmotic membrane barrier and thus allowing the photosensitizer to diffuse through the compromised cell membrane into the cell.

U.S. Pat. No. 5,616,342, to Lyons, purportedly discloses an emulsion comprising a lipid, a poorly water-soluble photosensitizing compound, a surfactant, and a cosurfactant. Poorly water-soluble photosensitizers are disclosed to pose serious challenges to achieving suitable formulation for administration to the body. Lyons '342 discloses that surfactants facilitate the preparation of the emulsion by stabilizing the dispersed droplets of an oil-in-water emulsion, and that the use of surfactants in combination with poorly water-soluble pharmacologic compounds is known in the art. Unlike the surface acting agents of the Applicant's present invention, the surfactant in Lyons does not produce a disorientation of a cell membrane so that the cell membrane no longer functions as an effective osmotic barrier.

Many hospitalized patients, particularly patients in an Intensive Care Unit ("ICU"), must be fitted with endotracheal tubes to facilitate their respiration. An endotracheal tube is an elongate, semi-rigid lumen which is inserted into a patient's nose or throat and projects down into airflow communication with the patient's respiratory system. As such, the patient either directly, or with the aid of a respiratory unit, is able to breathe more effectively through the endotracheal tube. Endotracheal tubes may remain in place within a patient for an extended period of time, e.g. up to a 14 day period. Biofilm contamination of endotracheal tubes within intubated patients may lead to an increased rate of infection, particularly pneumonia. An effective apparatus and method of use for eradication of biofilm organism on endotracheal tubes of intubated patients is desired.

Occurrences of catheter related bloodstream infection (CRBSI) have increased in part as a result of the wide use of invasive medical devices, including intravascular catheters. CRBSI is one of the most common types of nosocomial bloodstream infection, a finding that has been attributed to the wide use of intravascular catheters in hospitalized patients. Recent interventions to control CRBSI include anticoagulant/antimicrobial lock, use of ionic silver at the insertion site, employment of an aseptic hub model, and antimicrobial impregnation of catheters.

Several factors pertaining to the pathogenesis of CRBSI have been identified. The skin and hub are the most common sources of colonization of percutaneous vascular catheters. For short-term, non-nontunneled, noncuffed catheters, the organisms migrate from the skin insertion site along the intercutaneous segment, eventually reaching the intravascular segment of the tip. For long-term catheters, the hub is a major source of colonization of the catheter lumen, which ultimately leads to bloodstream infections through luminal colonization of the intravascular segment.

The catheter surface is another factor relating to the pathogenesis of CRBSI. Organisms that adhere to the catheter surface maintain themselves by producing an "extracellular slime," a substance rich in exopolysaccharides, often referred to as fibrous glycocalyx or microbial biofilm. Microorganisms bind to the surface of host proteins, such as fibrin and fibronectin, to produce biofilm. As described in more detail herein, the organisms embed themselves in the biofilm layer, often becoming more resistant to antimicrobial activity. The use of lumen flush solutions including a combination of antimicrobial agents as well as anti-coagulants is a known process. Another strategy has been to impregnate the surfaces of catheters with antimicrobial agents in order to prevent colonization and the formation of biofilm. An improved approach for prevention of intravascular catheter-related infections is desired.

A considerable amount of attention and study has been directed toward preventing colonization of bacterial and fungal organisms on the surfaces of orthopedic implants by the use of antimicrobial agents, such as antibiotics, bound to the surface of such devices. The objective of such attempts has been to produce a sufficient bacteriostatic or bactericidal action to prevent colonization. Various methods have previously been employed to coat the surfaces of medical devices with an antibiotic.

U.S. Pat. No. 4,442,133, invented by Greco et al., discloses a method to coat the surface of medical devices with antibiotics involving first coating the selected surfaces with benzalkonium chloride followed by ionic bonding of the antibiotic composition. Applicant incorporates by reference herein the teachings of U.S. Pat. No. 4,442,133.

U.S. Pat. No. 4,879,135, invented by Greco et al., discloses surface modification of surgical implants by binding of drugs which, after implantation, are slowly released. More particularly, the invention relates to improved surgical implants having sustained, localized delivery of pharmacological agents such as extended antibiotic activity or reduced thrombogenicity, and methods for producing same. The surface modification of surgical implants by the adhesion thereto of pharmacological agents for the purpose of minimizing infection and prosthesis rejection is well-known and has generated broad interest for some time. Applicant incorporates by reference herein the teachings of U.S. Pat. No. 4,879,135. Many different approaches have been taken including those disclosed in U.S. Pat. Nos. 4,563,485; 4,581,028; 5,707,366; and 4,612,337, each being incorporated by reference herein.

A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing. The National Institutes of Health estimates that the formation of biofilms on heart valves, hip and other prostheses, catheters, intrauterine devices, airway and water lines and contact lenses has become a $20 billion dollar health problem in the United States. A treatment apparatus and protocol for the reduction and/or eradication of biofilms is another aspect of the present invention.

Biofilms are remarkably resistant to treatment with conventional topical and intravenous antimicrobial agents. The Center for Biofilm Engineering at Montana State University has reported that biofilms may require 100 to 1,000 times the standard concentration of an antibiotic to control a biofilm infection. This is thought to be due to the antibiotic's inability to penetrate the polysaccharide coating of the biofilm. Even more concerning is that biofilms increase the opportunity for gene transfer due to the commingling of microorganisms. Such gene transfer may convert a previous avirulent commensal organism into a highly virulent and possibly antibiotic resistant organism.

Bacteria embedded within biofilms are also resistant to both immunological and non-specific defense mechanisms of the body. Bacterial contact with a solid surface triggers the expression of a panel of bacterial enzymes that cause the formation of polysaccharides that promote colonization and protection of the bacteria. The polysaccharide structure of biofilms is such that immune responses may be directed only at those antigens found on the outer surface of the biofilm and antibodies and other serum or salivary proteins often fail to penetrate into the biofilm. Also, phagocytes may be effectively prevented from engulfing a bacterium growing within a complex polysaccharide matrix attached to a solid surface.

Nosocomial pneumonia is the most prevalent infection in patients who are mechanically ventilated. It is the leading contributor to mortality in patients, accounting for 50% of deaths in patients with hospital acquired infections. The endotracheal tubes (ET) and tracheostomy tubes have long been recognized as a risk factor for nosocomial pneumonia since they bypass host defenses allowing bacteria direct access to the lungs. These tubes are commonly made of polyvinyl chloride, a surface on which local bacteria colonize rapidly to form an adhesive polysaccharide glycocalyx layer. This glycocalyx layer protects bacterial colonies from both natural and pharmacologic antibacterial agents, in effect increasing the virulence of the bacterial species in the intubated host. This phenomenon of biofilm formation has been demonstrated to occur on ET tubes and subsequent dislodgement of biofilm protected bacteria in the lungs by a suction catheter is considered to be a significant factor in the pathogenesis of nosocomial pneumonia. Indeed, in a study of biofilm formation in endotracheal tubes, microbial biofilm was identified by surface electron microscopy in 29 of 30 endotracheal tubes examined. Interestingly, there was no biofilm formation on the outer surface of the ET tube. Biofilm formed exclusively on the luminal surface of all tubes regardless of whether the patients had received broad spectrum antibiotics and was most prevalent around the side hole of the tip region. ET tubes obtained within 24 hours of placement showed large areas of surface activity with adherent bacteria in a diffuse pattern indicating initial colonization of the ET tube. The surface of tubes in place for longer periods had a profuse microbial biofilm. In some instances a large mass of matrix enclosed bacterial cells appeared to project from the confluent accretion on the luminal surface of the ET tube in such a manner that it could be dislodged readily and aspirated into the lower respiratory tract. Pseudomonas species, *Staphylococcus aureus*, and enteric aerobic bacteria including *E. coli*, were the most frequently isolated pathogens in the ET tubes in patients that did not receive broad spectrum antibiotics. These also are the pathogenic bacteria most commonly found in nosocomial pneumonia. In patients that received broad spectrum antibiotics yeast species and Streptococcus species were more common. Evaluations have been made into the relationship of biofilm formation in endotracheal tubes and distant colonization of the pulmonary tree. These evaluations have demonstrated that bacteria from the endotracheal tube biofilm were capable of being cultured from the moisture exchanger and the ventilator tubing up to 45 cm from the tip of the endotracheal tube. Furthermore they demonstrated that contamination of the tracheal tube biofilm with a patient's own gastrointestinal flora provides a mechanism for initial and repeated lung colonization and secondary pneumonia. These life threatening pulmonary infections are perpetuated by microbiological seeding from the tracheostomy and endotracheal tube biofilms and become difficult to treat due to the propensity of the biofilm microorganisms to develop antibiotic resistance. Biofilm contamination of endotracheal tubes within intubated patients may lead to infections or other complications as a result of biofilm organisms.

Catheters used for abdominal cavity tubing drainage bags and various connectors are also common sources of infection. In particular, a high percentage of patients who require long-term urinary catheters develop chronic urinary tract infections. Such patients are at risk of developing bacteremia or chronic pyelonephritis, condition of high morbidity and mortality. Many different medical articles may lead to infection when in contact with a body tissue or fluid. Exemplary of such articles are vascular access (arterial and venous) catheters, introducers, vascular grafts, urinary catheters and associated articles, such as drainage bags and connectors, and abdominal cavity drainage tubing, bags and connectors. A novel apparatus and method of infection prevention for such medical articles is particularly desired.

A variety of air filtration devices are known. A need exists, however, for an air filtration device which can neutralize biological threats associated with warfare. A need also exists for an improved air filtration device for building HVAC systems, particularly within hospitals and other care facilities. In such settings, an efficient system or process is needed for the removal of bacteria and fungi, such as aspergillus. Desired applications include a portable systems (mask form) and non-portable systems (a building or other structure filter system, or a vehicle interior air filter system). Known electromagnetic radiation pathogen destruction techniques have significant limitations. For example, UV and microwave destruction approaches may only reduce the bacteria count, and not eradicate the pathogens altogether. Furthermore, bacteria may become resistant to UW eradication over relatively short periods of time. Microwave destruction is through generation of severe heat. This modality would not be applicable as a portable biological weapon countermeasure. In comparison, photodynamic therapy antibacterial effects have demonstrated complete destruction and sterilization of highly concentrated bacterial species in vitro and therefore would appear to be superior to the above methods. An improved air filtration/decontamination device for efficiently and effectively eliminating harmful biological elements such as viruses, bacteria, fungus, etc., from the air is particularly desired.

SUMMARY OF THE INVENTION

The present invention provides a method of photoeradication of cells and acellular organisms, such as during an in vitro or in vivo disinfection or sterilization procedure, or for cancer cell or acellular organism eradication. In one embodiment, the method utilizes a combination of a photosensitive material and a chemical agent, such as a surfactant material, in a solution. The invention additionally provides a method of dispensing a combined solution at or near the tissue site and subsequently irradiating the tissue site with light at a wavelength absorbed by the photosensitive material. The invention also relates to an apparatus or kit assembly including a surfactant material and a photosensitive material. Yet another aspect of the present invention is the eradication or destruction of biofilms via a photodynamic mechanism.

The invention also relates to a use of a photosensitizing material, such as methylene blue, methylene green, or toluidene blue, in combination with a surfactant compound, such as polymyxin B, SDS, cetrimide or benzalkonium chloride, in a PDT treatment protocol against bacterial, fungal, acellular organism infections, and/or for cancer cell photoeradication. A treatment device is configured to deliver light energy to the area of infection or cancer cell activity at wavelengths ranging from about 450 nm to about 850 nm; provide a dosage rate ranging from about 0 to about 150 mw/cm$^2$; and provide a light dose ranging from 0 to about 300 J/cm$^2$.

The use of a photosensitive material, such as methylene blue, methylene green, or toluidene blue, combined with a surfactant material, such as SDS, polymyxin B, cetrimide or benzalkonium chloride, in a photodynamic therapy advantageously acts as a broad spectrum antimicrobial, i.e., antibacterial, antiviral, sporicidal, and/or antifungal agent. The photosensitizer/surfactant combination and PDT may be used, for example, before a surgical operation. The present invention advantageously results in the destruction of gram positive and gram negative bacteria, fungi, viruses, and spores. Importantly, the present invention acts to destroy antibiotic resistant bacteria as it utilizes a different destruction mechanism than antibiotics.

The invention also relates to a method of treating an infection including identifying an in vitro or in vivo area of infection; applying or dispensing a concentration including a photosensitive material, such as methylene blue, methylene green, or toluidene blue, and a surfactant, such as polymyxin B, SDS, cetrimide or benzalkonium chloride, to the area of infection; and exposing the area of infection with a light having a light wavelength, light dosage and a light dosage rate. For toluidene blue, the light wavelength may range from about 560 nm to about 680 mn. For methylene blue, the wavelength may range from about 600 nm to about 670 mn. For methylene green, the wavelength may range from about 600 nm to about 670 nm. The light dosage may range from about 10 J/cm$^2$ to about 60 j/cm$^2$. The light dosage rate may range from about 50 mw/cm$^2$ to about 150 mw/cm$^2$. The concentration for methylene blue, methylene green, and toluidene blue may range from about 10 μg/ml to about 500 μg/ml. For other photosensitive materials, the preferred wavelength or range may be known or available. The area of infection may include gram positive and gram negative bacteria, fungus, spores, or viruses including, but not limited to, at least one of Staphylococcus sp., *Candida albicans, Escherichia coli*, Enterococcus sp., Streptococcus sp., Klebsiella, Serratia, *Pseudomonus aeruginosa, Hemophilus influenzae*, Clostridia sp., Herpes strains, or human immunodeficiency virus (HIV).

The invention also relates to a treatment kit having a solution including at least a combination of a photosensitizing material, such as methylene blue, methylene green, or toluidene blue, and a surfactant material, such as polymyxin B, SDS, cetrimide, or benzalkonium chloride. For polymixin B, the concentration ranges may be from about 3 μg/ml to about 500 μg/ml. For SDS and cetrimide, the concentration range may be from 0.005% to 1%. For benzalkonium chloride, the concentration ranges may be from 0.001% to 1%. A particular concentration range of interest for benzalkonium chloride is from 0.005% to 0.5%. A laser light emitting treatment device may be utilized to effect the photodynamic process, including but not limited to a light source which emits at wavelengths ranging from about 450 nm to about 850 nm; providing a dosage rate ranging from about 10 mw/cm² to about 150 mw/cm²; and providing a light dose ranging from 5 J/cm² to about 300 j/cm². Alternative light sources would also be practicable as appreciated by one skilled in the relevant arts, including but not limited to non-coherent light sources, such as flash bulbs and high intensity lamps.

The invention also relates to a method of treating an infection, an in vitro or in vivo sterilization procedure, or photoeradication of cancer cells, including the steps of providing one or more cells; providing a concentration of combined photosensitive material/surfactant on or near the one or more cells; and applying a light having a wavelength ranging from about 450 nm to about 850 nm; a dosage rate ranging from about 0 to about 150 mw/cm²; and a light dose ranging from 0 to about 300 J/cm² to the one or more cells wherein the combination of light and photosensitive material is adapted to cause photodestruction of the one or more cells. The one or more cells may be an infection caused by or associated with a bacteria, virus, or fungus. Alternatively, the one or more cells may be cancer cells. Virus infected cells may also be treated in accordance with the present invention. In such instance, a virus within the cell may be specifically eradicated without destruction of the host cell. Obligate intracellular bacterial agents, such as Chlamydia, Rickettsia, and Ehrlichia, may be treated in accordance with the present invention. Other bacteria may also be treated in accordance with the present invention. The one or more cells may be gram positive or gram negative bacteria. The photosensitive material may be methylene blue, methylene green, toluidene blue, or a combination thereof. The photosensitive material may be monomeric, dimeric, or polymeric.

Another aspect of the present invention is a photodynamic method of biofilm reduction and/or eradication on medical articles. A wide variety of medical articles may be utilized to practice aspects of the present invention. Such articles may include implants (temporary or permanent), endotracheal tubes, catheters (venous and arterial), grafts, shunts, heart valves, orthopedic prostheses, intraocular prostheses, profusion pumps, sutures, and associated articles, such as connectors and tubing. A particular aspect of the present invention is to provide an effective apparatus and method of use for eradication of biofilm organism on endotracheal tubes within intubated patients.

Yet another object of the present invention is the provision of an improved endotracheal tube having a surface coating or surface impregnation of a photosensitive material and a surfactant, such as benzalkonium chloride. The improved endotracheal tube is utilized in a photodynamic process to eradicate organism upon the tube surface. The endotracheal tube may be in light communication with a light source, such as a local fiber optic device or a remote light source. In one embodiment, the improved endotracheal tube is formed of a light communicative material such that light is able to pass through at least portion of the tube and illuminate a cell site. In one embodiment, the tube provides general light communication from an external light port to a tube surface cell site which is within the patient. Alternative medical prostheses may utilize teachings of the present invention to photodynamically eradicate organisms upon the prostheses.

Methylene blue (MB) based photodynamic therapy has been demonstrated in vitro and in vivo to be effective in the photoeradication of some antibiotic resistant gram positive and gram negative bacteria. In general, methylene blue based photodynamic therapy has limited applicability toward destruction of gram negative bacteria. Methylene blue has a very low tissue toxicity and can be administered to humans orally and intravenously in high doses without any toxic effects. Because of the known low toxicity and its present use and acceptance in medical practice as well as its high photoactive potential this photosensitive material is ideal use in accordance with the present invention for evaluation of its effect on the destruction of bacteria, viruses and fungi. The photoactive dye methylene blue belongs to the phenothiazine class. Its bactericidal effect is related to its photodynamic properties. This dye is a single pure compound and has a strong absorption at wavelengths longer than 610 nm, where light penetration into tissue is optimal. The absorbance peaks of MB are at 611 nm and 664 nm, its optical extinction coefficient is 81600 $M^{-1}$ $cm^{-1}$. MB has a high quantum yield of the triplet state formation (~T=0.52-0.58) and a high yield of the singlet oxygen generation (0.2 at pH 5 and 0.94 at pH 9).

The photoactivity of MB results in two types of photooxidations: (i) direct reaction between the photoexcited dye and substrate by hydrogen abstraction or electron transfer creating different active radical products; and (ii) direct reaction between the photoexcited dye in triplet state and molecular oxygen producing singlet oxygen. Both kinds of active generated products are strong oxidizers and they cause cellular damage, membrane lysis, protein inactivation and/or DNA modification.

Biofilms are resistant to topical, oral and intravenous antibiotic administration due to the polysaccharide glycocalyx formation that surrounds the bacteria. The polysaccharide coating prevents the antibiotic from penetrating into the biofilms and destroying the bacteria. Methylene blue has the potential ability to destroy biofilms as it selectively binds and penetrates polysaccharides thereby exposing the bacteria in the biofilm to the photodestructive effects of methylene blue. For this reason, methylene blue may be an ideal photosensitizer that may provide a means for the broad spectrum photoeradication of biofilms. The use of a surfactant, such as SDS or benzalkonium chloride, can act to both emulsify the biofilm and increase a membrane permeability of an acellular or cellular organism within the biofilm. The combination of a surfactant with a photosensitive material permits the photosensitive material to pass through the biofilm and acellular or cellular organism membrane, and accumulate within the acellular or cellular organism. As a result, a treatment protocol according to the present invention results in more effective eradication of acellular and cellular organsisms within biofilms.

Another object of the present invention is the provision of a treatment protocol utilizing a photosensitive material and surfactant in a pH-selective solution. By adjusting the pH of the solution, an enhanced kill rate of gram-negative or gram-positive bacteria results. The pH of the solution can be determined and adjusted using known processes or agents.

Another object of the present invention is the provision of an air filtration/decontamination device utilizing a photosensitive material and the surfactant, benzalkonium chloride, to eradicate acellular and cellular organisms via a photodynamic process. The photosensitive material and benzalkonium chloride may be provided in a solution. The combined solution may wet a filter media within the device. The photodynamic process may include light illumination of a wetted filter media to eradicate acellular and cellular organisms upon the filter media. An effective eradication of spores may be provided by such as device. The photodynamic air filtration device according to the present invention associates pathogens with a photosensitizer agent and benzalkonium chloride and subsequently illuminates the pathogen/photosensitizer/benzalkonium chloride combination to achieve photodynamic eradication. In one example, a rotating filter may be used to capture the pathogens and bring them into a photosensitizer/benzalkonium chloride solution. The photosensitizer solution may be selected from among a group of photosensitive materials. The pathogens and photosensitizer/benzalkonium chloride solution are subsequently illuminated by a light source, such as a VCSEL array, a laser diode array or an incandescent bulb. As a result, one aspect of the present invention concerns an air purification system utilizing photodyamic therapy (PDT) broad spectrum destruction of microbiological organisms. One significant application of the technology would be as a defense system against a biological weapons attack, as the broad spectrum destruction of bacteria, fungi (particularly, the aspergillus fungi group), and viruses would offer an increased level of protection. Additional suitable applications include: permanent or temporary building environments, vehicular applications, and portable mask form. Using a filtration device to capture airborne biological threats, PDT could be performed on the filter for eradicating the pathogen.

Biological weapons of significant concern include anthrax, tularemia, plague and small pox. The first three are gram positive and gram negative bacteria and small pox is a very large DNA virus. Based on research, these biological agents should be susceptible to eradication by photodynamic therapy treatment. Non-military uses are also practicable, for example, to eliminate or reduce the exposure of airborne pathogens present within commercial building HVAC systems.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawings and description are to be regarded as illustrative in nature, and not as restrictive.

BRIEF DESCRIPTION OF THE FIGURES

FIG. 1 is a tree structure of organisms.

FIG. 2 is a table of results of photodynamic eradication using a combined solution of methylene blue and the surfactant, benzalkonium chloride.

FIG. 3 is a table of results of photodynamic eradication of bacterial spores using methylene green and benzalkonium chloride.

FIG. 4 is a table of results of photodynamic eradication of microbial biofilm organisms upon a human endotracheal tubes using methylene blue and the surfactant benzalkonium chloride.

FIG. 5 is a depiction of an endotracheal tube within an intubated patient illustrated biofilm eradication aspects of the present invention.

FIG. 6 is a depiction of an air filtration/decontamination device utilizing a photodynamic reaction for organism eradication, using a photosensitive material and the surfactant, benzalkonium chloride.

DETAILED DESCRIPTION OF THE INVENTION

In accordance with the invention, a photodynamic therapy utilizes a photosensitive material, such as methylene blue, methylene green, or toluidene blue, in combination with a chemical agent, such as surface acting agent or 'surfactant', and a light emitting device, such as a light wand, light patch, light pad or shaped light-emitting or light-communicating article. As described in more detail herein, the photodynamic therapy may be achieved at a variety of cells sites, including but not limited to tissue fields and biofilms.

The photodynamic therapy according to the present invention may be utilized in the eradication of cellular organisms, such as tumor cells, cancer cells, virus-infected cells, bacteria, etc. The photodynamic therapy according to the present invention may also be utilized in the eradication of acellular organisms, defined broadly to include organisms not composed of cells, e.g., bodies of protoplasm made discrete by an enveloping membrane (also referred to a capsule, envelope, or capsid). Examples of acellular organisms include, but are not limited to, viruses, spores, and other virus-like agents such as viroids, plasmids, prions, and virinos, and other infectious particles.

Reference may be made to FIG. 1, wherein component structures of acellular and cellular organisms are presented. Procaryotic cells are cellular organisms, including bacteria. The component structures of procaryotic cells include appendages, cell envelope, and protoplasm. The cell envelope further includes the glycocalyx (capsules, slime layers), cell wall, and cell membrane. All bacteria cells invariably have a cell envelope, glycocalyx, cell membrane, cell pool, ribosomes, and a nucleoid; the majority have a cell wall. Although they are common to many species, flagella, pili, fimbriae, capsules, slime layers, and granules are not universal components of all bacteria. Organisms of the genera Chlamydia, Rickettsia, and Ehrlichea, referred to as obligate intracellular bacteria, are prokaryotes that differ from most other bacteria with respect to their very small size and obligate intracellular parasitism.

Eucaryotic cells are typical of certain microbial groups (fungi, algae, protozoans, and helminth worms) as well as all animal and plant cells. Eucaryotic cells have component structures including appendages, surface structures, cell wall, cytoplasmic membrane, nucleus, cytoplasm, cytoskeleton, and ribosomes. The surface structures may include glycocalyx, capsules, and slimes. Virus particles are not cells and they neither possess procaryotic nor eucaryotic structural qualities. Instead, they are large, complex macromolecules, with parts made up of repeating molecular subunits. Virus particles include component structures of a covering and a central core. The covering includes a capsid and in some viruses, an envelope. All viruses have a protein capsid or shell that surrounds the nucleic acid strand. Members of 12 of the 17 families of animal viruses possess an additional covering external to the capsid called an envelope, which is actually a modified piece of the host's cell membrane. Viruses that lack this envelope are considered naked nucleocapsids. Special virus-like infectious agents include the prion (proteinacious infectious particles) and viroids.

A photosensitive material is defined herein as a material, element, chemical, solution, compound, matter, or substance which is sensitive, reactive, receptive, or responsive to light energy. Photosensitive materials may be provided in a liquid, gaseous, or solid form, including but not limited to liquids, solutions, topical ointments, or powders. Photosensitive materials for use in accordance with the present invention are generally non-toxic to the target cellular or acellular organisms and surrounding tissues at concentrations envisaged. However, there is no particular requirement that the photosensitive material should be non-toxic to the microbes. Particular photosensitizers which may be used in accordance with the invention include dyes and compounds such as methylene blue, methylene green, and toluidene blue.

The terms "chemical agent" and "surface acting agents" and "surfactants" as used herein are broadly defined to include materials, compounds, agents, chemicals, solutions, or substances which alter the energy relationships at molecular interfaces. Among the manifestations of these altered energy relationships is the lowering of surface or interfacial tensions. Chemical agents or compounds displaying surface activity are characterized by an appropriate structural balance between one or more water-attracting groups and one or more water-repellent groups. Surfactants are characterized by having two different moieties, one polar and the other nonpolar. The polar moeity is referred to as hydrophilic or lipophobic, and the nonpolar as hydrophobic or lipophilic. The electrical charge on the hydrophilic portion of a surface acting agent may serve as a convenient basis of classification of these compounds. Surface active agents have been classified as: Anionic, Cationic, Non-Ionic, and Amphoteric. Other classes of surfactants are also known or may be developed or defined in the future. Chemical agents, such as surfactants, are known to affect the permeability of cell membranes, and membrane-like structures of acellular organisms, such capsids and envelopes. The ability of these chemical agents or surfactants to become oriented between lipid and protein films is thought to produce a disorientation of the membrane of microorganisms, so that it no longer functions as an effective osmotic barrier. The term 'membrane' as used herein is meant to broadly include cellular or acellular organism structures, such as cell walls, cytoplasmic membranes, cell envelopes, coverings, capsids, envelopes, or other types of boundary-defining terms of cellular or acellular organisms. It is believed that a photosensitive material may diffuse through the membrane of a microorganism having a surfactant-compromised membrane. A photosensitive material concentration within the membrane and the organism increases over time via osmotic diffusion of the photosensitive material across the surfactant-compromised membrane.

The polymixins, colisimethate, and the polyene antifungal agents nystatin and amphotericin are surfactants, as is sodium dodecyl sulfate (SDS). Cetrimide is also a known surfactant. Benzalkonium chloride, having synonyms of n-alkyl dimethyl benzyl ammonium chloride solution, parasterol, alkyl dimethyl benzylammonium chloride, and zephiran chloride, is also a known surfactant. Benzalkonium chloride is a cationic surfactant, having a known use as a medical disinfectant.

A light source is utilized to practice embodiments of the present invention. The light source may be laser light source, a high intensity flash lamp, light emitting diode (LED) or other illumination sources as appreciated by those skilled in the relevant arts. A broad spectrum light source may be utilized, however a narrow spectrum light source is one preferred light source. The light source may be selected with reference to the specific photosensitive material, as photosensitive materials may have an associated range of photoactivation. A laser light source may be used to practice the present invention. A variety of laser light sources are currently available, and the selection of a particular laser light source for implementing the PDT would readily be appreciated by those skilled in the relevant arts. A laser source may be selected with regard to the choice of wavelength, beam diameter, exposure time and sensitivity of the cellular and/or acellular organisms to the laser/photosensitizer/surfactant combination. In preferred embodiments, the light source is utilized for a period of time necessary to affect a photodynamic response. The period of time for photodynamic activation of the photosensitive material is preferably between 5 seconds and 1 hour. Yet more preferably, the period of time for light illumination is between 2 and 20 minutes.

A variety of light delivery devices may be utilized to practice the present invention. A hand manipulable light wand or fiber optic device may be used to illuminate tissue within a living body. Such fiber optic devices may include a disposable fiber optic guide provided in kit form with a solution containing a photosensitive material and a surfactant. Other potential light devices for use in accordance with the present invention include the devices disclosed in applicant's U.S. Pat. No. 6,159,236, entitled *Expandable treatment device for photodynamic therapy and method of using same*, and U.S. Pat. No. 6,048,359, entitled *Spatial orientation and light sources and method of using same for medical diagnosis and photodynamic therapy*, both incorporated in their entireties by reference herein. Yet another light delivery scheme is envisioned herein, wherein a medical device or prosthesis is utilized to communicate light from an external light source to a cell site within a patient, particularly a biofilm cell site on a surface of the prosthesis. A translucent or transparent prosthesis body may be provided to receive light at a first location and communicate light to interior surfaces which support a biofilm. A variety of light communication schemes utilizing at least a portion of the prosthesis body are envisioned.

Repeat administrations of a treatment protocol may also be necessary or desired, including repeat administrations of surfactants and photosensitive materials and light activation. The repeat administrations may include different surfactants and/or photosensitive materials than previously administered. Repeat administrations of the treatment protocol may continue for a period of time.

Additional aspects of the present invention include administration or delivery approaches of the photosensitive material and the surfactant. In one example, the photosensitive material and the surfactant are provided in a combined solution and topically applied to the cell site. In alternative embodiments, the photosensitive material may be applied or delivered or dispensed to a tissue or cell site before, during, or after the application or delivery of the surfactant through known delivery/administration approaches. In one preferred embodiment, a topical surfactant application would precede a topical photosensitive material application by 1-30 minutes.

Additional aspects of the present invention further include a prosthesis or other medical product, wherein the prosthesis has a solution or compound including one or both of a photosensitive material and a surfactant, such as benzalkonium chloride, provided at or near a surface of the prosthesis, particularly at a surface capable of supporting a biofilm. The solution or compound may be provided at or near the surface of the prosthesis via known bonding or impregnation techniques, or may be provided during other manufacturing steps of the product. The term "prostheses" employed herein and throughout the specification and claims is intended to broadly include, though not be limited to, devices used to replace or assist a body part or bodily function, including:

Intravenous, peritoneal dialysis, parenteral and urological catheters;
Endotracheal tubes or respiration related devices;
Vascular grafts;
Ventricular and peritonovenous shunts;
Heart valves;
Orthopedic prostheses;
Intraocular prostheses;
Profusion pumps;
Sutures;
Prostheses used in reconstructive plastic surgery; and
Implantable devices.

A photodynamic eradication of organisms upon a prosthesis surface may be achieved by light illumination via a light source such as a laser, LED light, VCSEL device, flash bulbs, lamps, etc. Photodynamic eradication of organisms upon a prosthesis surface may be via internal illumination of the prosthesis using an remote light source. In envisioned embodiments, the prosthesis may be a transparent or translucent material for internally communicating light to a chemically-treated (photosensitive material and surfactant) surface of the prosthesis.

Additional aspects of the present invention further include combinations of different photosensitive materials and different chemical agents or surfactants during a treatment protocol. In one preferred embodiment, a particular combination of a photosensitizer and a surfactant would be dispensed to the tissue site in association with a first photodynamic illumination of the tissue site. After a period of time, another different particular combination of a photosensitizer and a surfactant would be dispensed to the tissue site in association with a second photodynamic illumination of the tissue site. Yet other aspects of the invention include combining a plurality of different surfactants with a given photosensitive material, and/or combining a plurality of different photosensitive materials with a given surfactant.

In another preferred embodiment, a photosensitive material such as methylene blue, methylene green, or toluidene blue may be used in combination with surfactants, such as SDS, polymyxin B, Arguard™, cetrimide, or benzalkonium chloride, and activated by light energy to provide broad spectrum antibiotic activity for destroying both gram positive and gram-negative bacteria, funguses, viruses, spores, and/or cancer cells. The photosensitive material and surfactant may be combined in solution and administered to a site to be treated. Solution administration may include topical application, inhalation, and/or intravenous, subcutaneous, intratumoral, or peritumoral injection. The photosensitive material and surfactant may also be provided via a chemical release from an impregnated surface of a medical article. Other surface binding approaches may be appreciated for associating the photosensitive material and the surfactant at a surface of the medical article. Additional administration approaches may also be practicable. An intratumoral injection of the solution may be advantageous for photoeradication of tumor cells.

Figure 1:
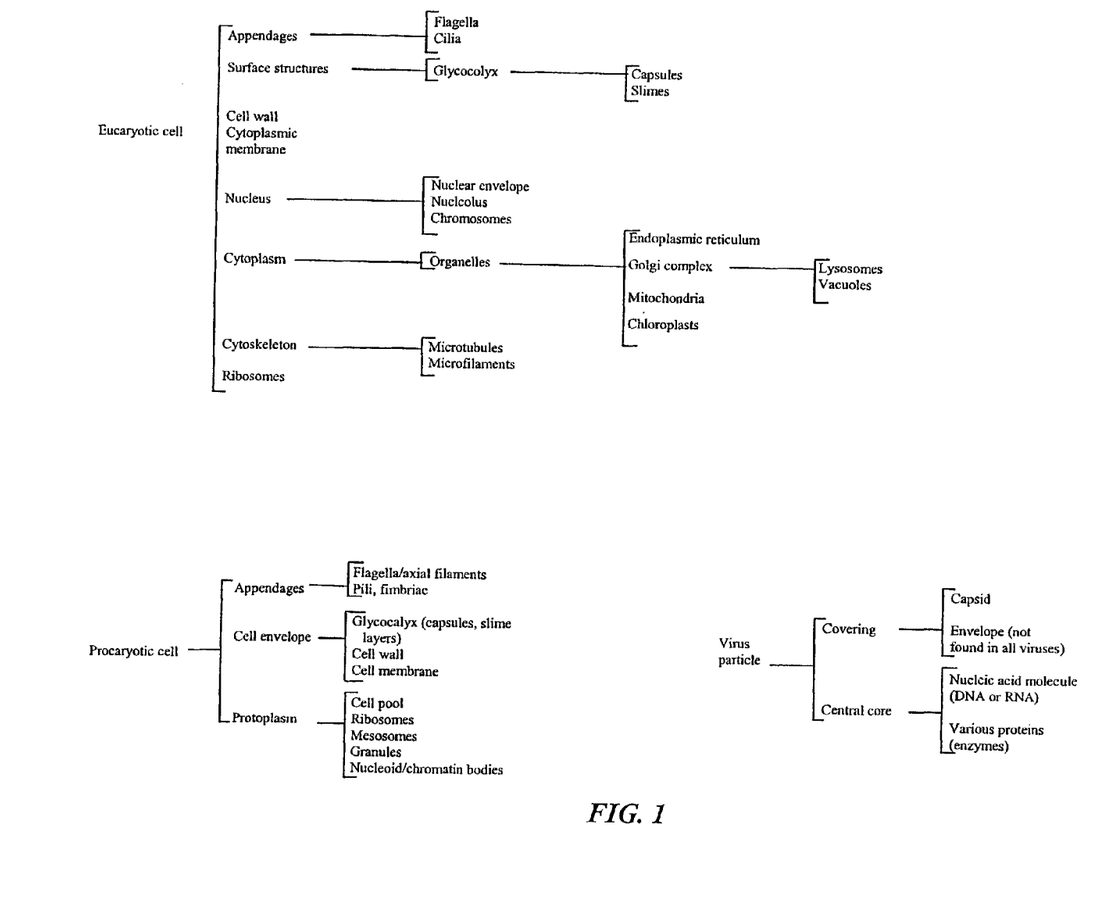
Figure 2:
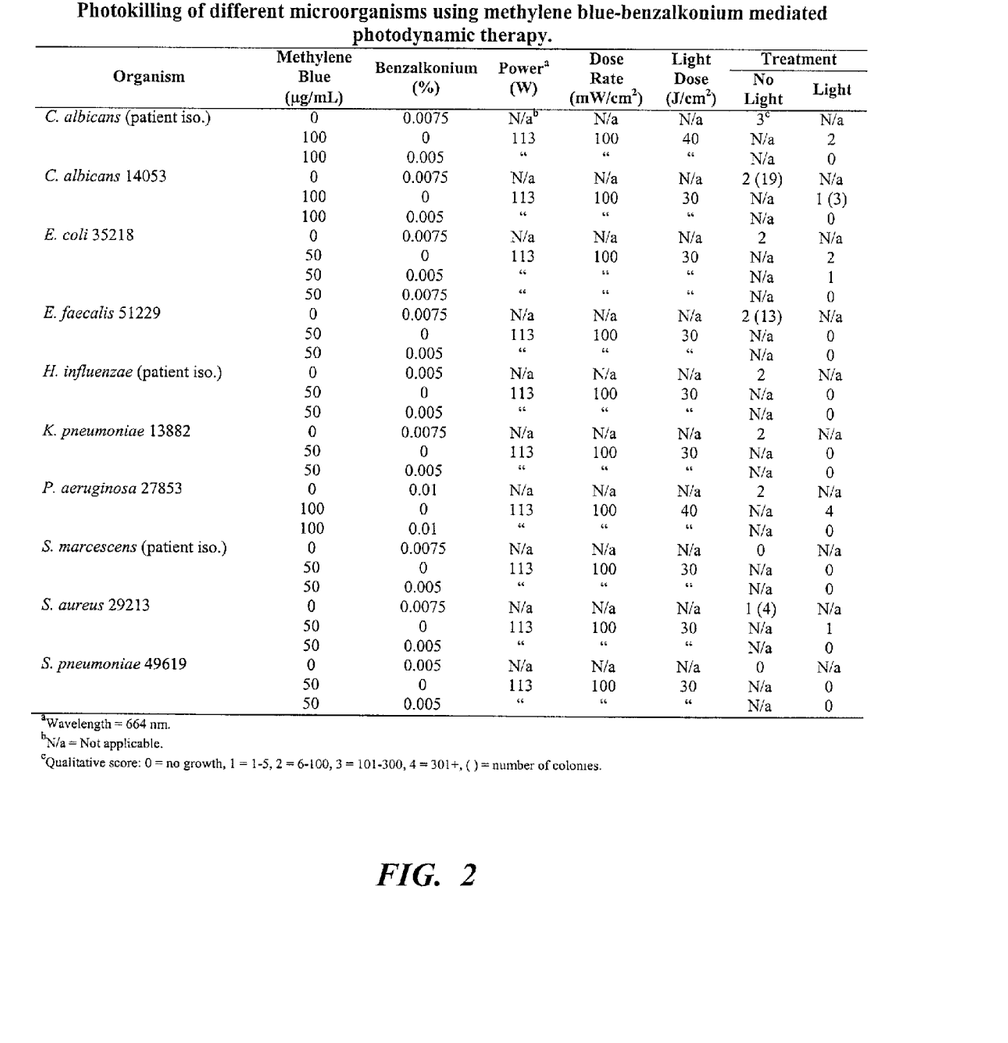

One particular treatment protocol according to the present invention utilizes the photosensitive material methylene blue and surfactant benzalkonium chloride. Benzalkonium chloride concentrations from 0.001% to 0.5% have been identified as advantageous in the destruction of certain microorganisms, such as *Candida albicans, Escherechia coli, Pseudomonas aeruginosa, Staphylococcus aureus*, Klebsellia, Serratia, *Haemophilus influenza,* and *Streptococcus pneumoniae*. Reference may be made to FIG. 2, which illustrates a schedule of investigation results. The inquiry was made into photoeradication using methylene blue mediated PDT and the surfactant benzalkonium chloride, at a wavelength of approximately 664 nm. The laser used for illumination was a diode laser. Methylene blue concentrations ranged from 0 to 100 µg/ml. Benzalkonium chloride concentrations ranged from 0 to 0.01%. The combined solution was topically applied at the cell site. A light dosage rate was 100 mw/cm². Light dosages ranged from 30 to 40 J/cm². A qualitative colony count relates particular colony counts to an associated score. For instance, a qualitative colony count of 5 would yield a score of '1', while a colony count of 151 would have an associated score of '3'. The results of this investigation demonstrated that the solution including a surfactant and a photosensitising agent sensitized several species of bacteria to killing by laser irradiation, though alone neither the surfactant nor the photosensitizing agent sensitized the bacteria to killing by laser irradiation. As a result, one particularly efficacious treatment for eradicating a microorganism according to the present invention may include the steps of disposing a solution containing a methylene blue and benzalkonium chloride at a tissue site and illuminating the tissue site with a light source effective to initiate a photodynamic therapy.

Figure 3:
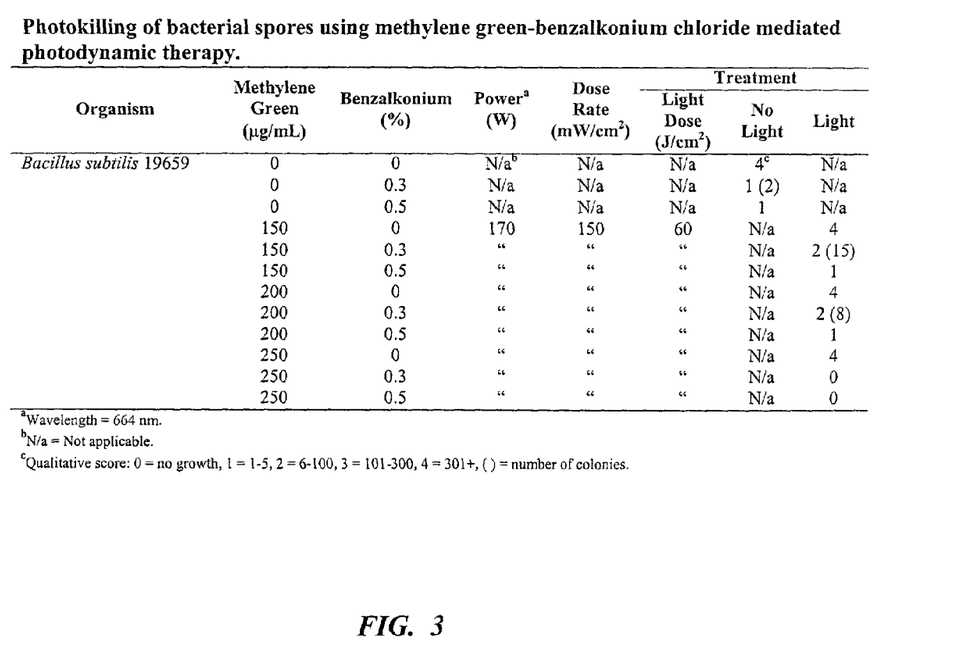

Reference may also be made to FIG. 3, which illustrates a schedule of results for an investigation according to the present invention. The inquiry was made into photoeradication of bacterial spores using methylene green mediated PDT and the surfactant benzalkonium chloride, at a wavelength of approximately 664 nm. Methylene green concentrations ranged from 150 to 250 µg/ml. Benzalkonium chloride concentrations ranged from 0 to 0.5%. The combined solution was topically applied at a cell site. Light dose rate was 150 mW/cm². Cultures were assessed: (i) without light illumination; and (ii) with light illumination. A qualitative colony count relates particular colony counts to an associated score. For instance, a qualitative colony count of 5 would yield a score of '1', while a colony count of 151 would have an associated score of '3'. The results of this investigation demonstrated that the solution including benzalkonium chloride and methylene green sensitized bacterial spores to killing by laser irradiation. As a result, an efficacious treatment for eradicating bacterial spores would include the steps of disposing a solution containing a methylene green and benzalkonium chloride at a tissue site and illuminating the tissue site with a light source effective to initiate a photodynamic therapy.

Known photosensitive materials which may find applicability in practicing the present invention include, but are not limited to, the following:

| PHOTOSENSITIVE MATERIAL | WAVELENGTH |
| --- | --- |
| Hypiricin | 550-660 nm |
| Aluminum phthalocyanine | 670-675 nm |
| Merocyanine | 500-560 nm |
| Psoralen | 320-400 nm |
| Rose Bengal | 548 nm |
| Acridine orange | 489 nm |
| Indocyanine green | 660 nm |
| Nile blue | 628 nm |
| Nile red | 553 nm |
| Toluidene | 560-660 nm |
| Methylene green | 600-670 nm |
| Lutetium Texaphyrin | 732 nm |
| Benzporphyrin derivative | 690 nm |
| Foscan (mTHPC) | 652 nm |
| Tin ethyl etiopurpurin | 664 nm |
| Photofrin (porfimer solution) | 630 nm |
| Aminolevulinic Acid | 630 nm |

Another aspect of the present invention is the provision of biofilm reduction and/or eradication. A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing.

The use of a surfactant, such as SDS or benzalkonium chloride, in combination with a photosensitive material, such as methylene blue or methylene green, is useful in treating biofilms. It is believed that by penetrating and emulsifying the protective glycocalyx and allowing the photosensitive material to penetrate into the biofilm and accumulate proximate to the embedded microorganisms, an increased diffusion of the photosensitizer into the microorganisms may be achieved. An increase in the diffusion rate into the microorganisms is further believed to facilitate a broad spectrum photodestruction of the biofilm and/or embedded microorganisms.

Biofilms are a serious and ever increasing health problem with limited ability at this time to effectively treat them. The development of a prototype topical methylene blue and benzalkonium chloride and light application system for the prevention and/or photoeradication of biofilms in endotracheal tubes, tracheostomy tubes, airway lines and indwelling catheters would greatly impact and reduce both the significant rate of nosocomial pneumonias and other catheter related infections but also reduce the ever increasing rate of antimicrobial resistance. As a result, one particularly efficacious treatment for eradicating a microorganism of a biofilm according to the present invention may include the steps of disposing a solution containing a methylene blue and benzalkonium chloride at a cell site and illuminating the cell site with a light source effective to initiate a photodynamic therapy.

Figure 4:
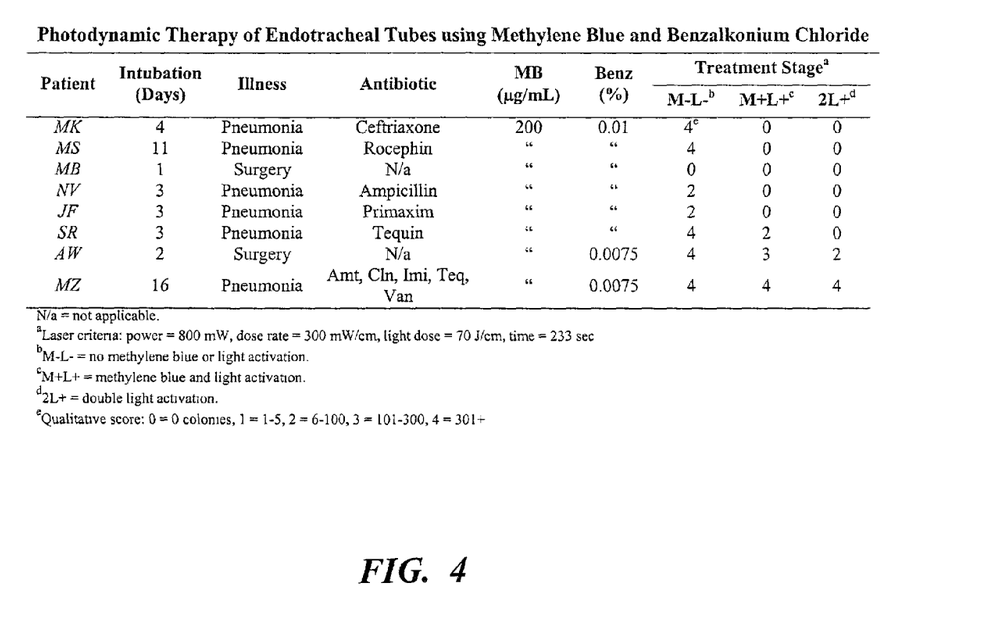

FIG. 4. illustrates a schedule of results for a biofilm microorganism eradication of human endotracheal tubes. The inquiry was made into photoeradication using methylene blue mediated PDT and the surfactant benzalkonium chloride, at a wavelength of approximately 664 nm. Methylene blue concentrations were 200 µg/ml. Benzalkonium chloride concentrations ranged from 0.0075% to 0.01%. Light dose was 70 J/cm. Light dose rate was 300 mW/cm. Time of illumination was 233 sec. Cultures were assessed: (1) without benzalkonium chloride, without methylene blue, and without light (M−L−), (ii) with benzalkonium chloride, with methylene blue, and a first application of light (M+L+), and (iii) with benzalkonium chloride, with methylene blue, and with a first and second applications of light (2L+). A qualitative colony count (as in FIGS. 2 and 3) relates particular colony counts to an associated score. For instance, a qualitative colony count of 5 would yield a score of '1', while a colony count of 151 would have an associated score of '3'. The results of this investigation demonstrated that the solution including benzalkonium chloride and methylene blue sensitized all organisms to killing by laser irradiation, including antibiotic resistant organisms. As a result, an efficacious treatment for biofilm microorganisms would include the steps of disposing a solution containing a photosensitive material, such as methylene blue, and a surfactant, such as benzalkonium chloride, upon the biofilm and illuminating the biofilm with a light source effective to initiate a photodynamic therapy.

Another preferred embodiment of the present invention provides a method of eradicating organisms at a tissue field includes the following steps of: (i) topically applying a solution containing 0.001% to 1% benzalkonium chloride and 50-500 µg/ml toluidene blue, methylene green, or methylene blue; and (ii) illuminating the tissue field with a light having a light wavelength, light dosage and a light dosage rate. The light wavelength may range from about 610 nm to about 680 nm. The light dosage may range from about 10 J/cm$^2$ to about 60 j/cm$^2$. The light dosage rate may range from about 50 mw/cm$^2$ to about 150 mw/cm$^2$. Alternative administrations for the solution containing benzalkonium chloride and a photosensitive material may include a local injection, inhalation, a transdermal patch, or an intravenous injection. A combination of different administrations may be utilized for a given treatment protocol. Alternative photosensitive materials for use with benzalkonium chloride may also be practicable. Alternative surfactants may also be practicable. A combination of different photosensitive materials and/or surfactants may be utilized for a given treatment protocol. A similar method may be utilized to eradicate viruses, or virus-infected cellular organisms without eradicating the host cellular organism.

Yet another aspect of the present invention is the use of a photosensitive material and a surfactant as a broad spectrum cellular and acellular organism agent for sterilizing medical equipment and prostheses, such as intravascular catheters, endotracheal tubes, catheters, and endoscopes, from viruses, bacteria, fungus, and spores. A particular application of a sterilization process may include the steps of: (i) providing or disposing a photosensitive material and benzalkonium chloride on or upon a tangible apparatus; and (ii) illuminating the apparatus with light at an appropriate wavelength and light dosage to effect a photodynamic reaction for eradicating the cellular and acellular organisms. Benzalkonium chloride concentrations may range from 0.001% to 1%. A more preferred range of benzalkonium chloride concentration would be between 0.005% to 0.05%.

One method of practicing the invention may include sterilization of medical equipment, such as an endotracheal tube, intravascular catheters, via biofilm eradication including the steps of: (i) providing a photosensitive material, such as methylene blue, methylene green, toluidene blue, etc., and a surfactant, such as SDS, cetrimide, ARGUARD, or benzalkonium chloride, on surfaces of the endotracheal tube having biofilm contamination; and (ii) illuminating the endotracheal tube with light at an appropriate wavelength and light dosage to effect a photodynamic eradication of cellular and/or acellular organisms in the biofilm. It is envisioned that additional combinations of photosensitive material and surfactant may be utilized to practice this application of biofilm / surface organism eradication.

Figure 5:
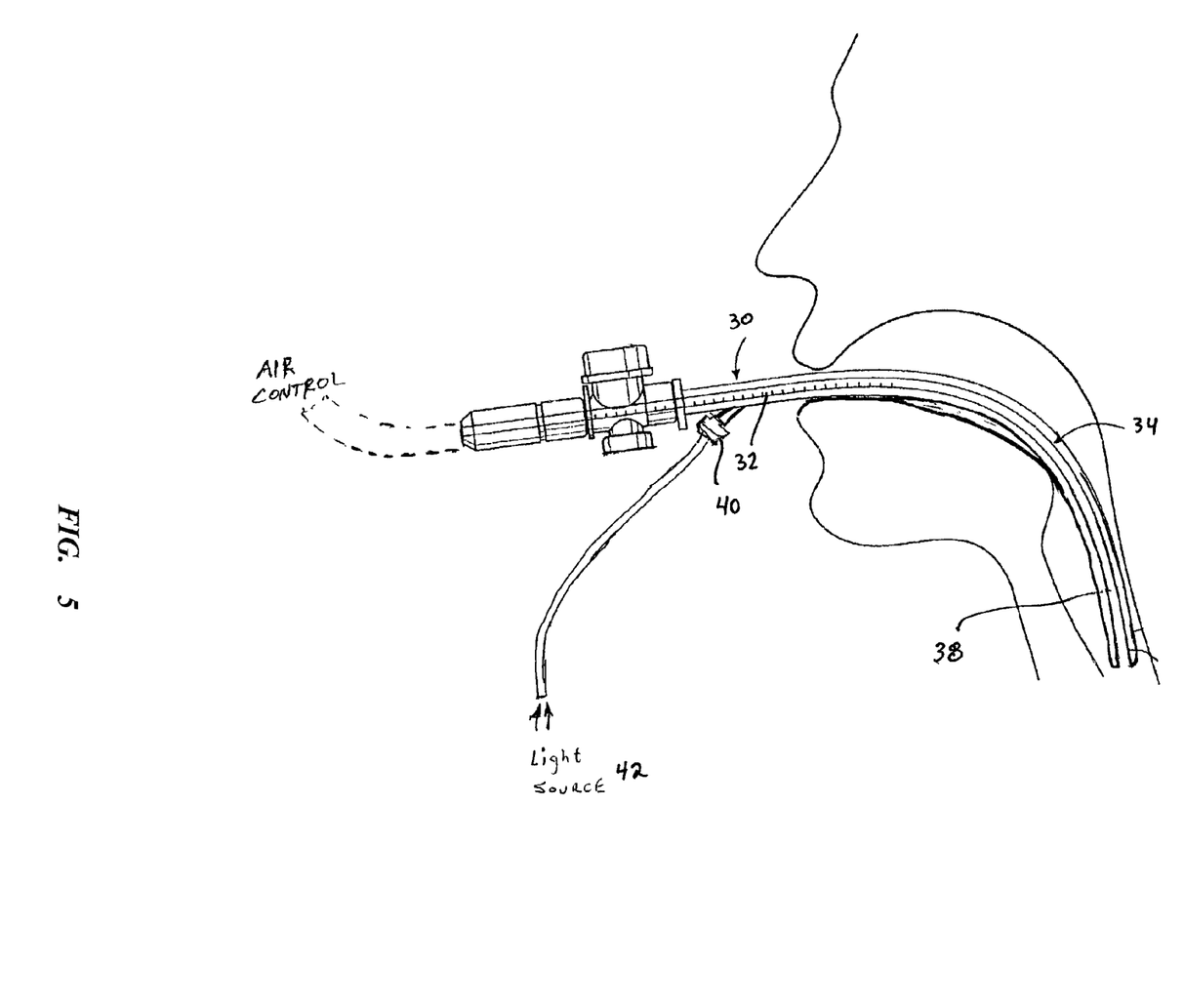

Another aspect of the present invention is directed toward an endotracheal tube disinfection apparatus and method of use. Endotracheal tubes are well known to those skilled in the relevant arts. In particular, an endotracheal tube 30 utilized to enable a patient to breathe is generally inserted down the throat of a patient as illustrated in FIG. 5. Such an endotracheal tube 30 is preferably of the type including an air flow passage 32 having an interior wall surface 34 that defines its interior diameter. In one embodiment of the present invention, the endotracheal tube 30 is formed from a translucent or transparent material capable of communicating light from a light source to a cell site 38. Surfaces of the endotracheal tube may have a photosensitive material and/or a surfactant, such as benzalkonium chloride, impregnated thereupon or bonded thereto. Those skilled in the relevant arts would appreciate the known surface impregnation or bonding techniques toward such end.

The cell site 38 may be a biofilm layer disposed on surfaces of the endotracheal tube 30, such as the tube lumen. A surface-released photosensitive material and surfactant may be utilized to achieve a photodynamic reaction at the cell site 38. In this regard, the photosensitive material and surfactant are released from the surfaces of the endotracheal tube and associate with organisms of the biofilm. A photodynamic eradication of organisms within the biofilm matrix may then be achieved by illuminating the biofilm organisms with appropriate light. In one embodiment as illustrated in FIG. 5, the endotracheal tube 30 may includes a light port 40 for coupling a light source 42 to the tube 30 wherein the tube body is capable of communicating light from the source 42 to the cell site 38. In an alternative embodiment, the endotracheal tube 30 may include a port (not shown) for receiving a fiber optic line having a light emitting end, wherein the fiber optic line is passed within the interior lumen of the tube to position the light emitting end at a location proximate the biofilm cell site.

In alternative embodiments, the combination of a photosensitive material and a surfactant may be provided in solution and disposed at the cell site 38 in a variety of manners, such as via a fluid line 46 or other fluid structure communicating the solution from a source 48 to a surface of the endotracheal tube (See, FIG. 5). Alternatively, a solution containing a photosensitive material and a surfactant may be communicated within an interior structure of the endotracheal tube 30 and be transferred to the biofilm matrix of the cell site 38 via one or more apertures (not shown) in the tube 30 wall.

A method of endotracheal tube photodynamic eradication of biofilm organisms on an intubated patient may include the steps of:
- providing an endotracheal tube having light communicative properties within the patient, wherein one or more surfaces of the tube have an associated photosensitive material and a surfactant;
- allowing the photosensitive material and surfactant to be released from the tube surfaces and react with the biofilm organisms;
- providing a source of light illumination having predetermined light characteristics; and
- illuminating the biofilm layer with the light source to achieve a photodynamic reaction resulting in the eradication of organisms within the biofilm layer.

The process as described above may be periodically repeated to photodynamically eradicate organisms upon the endoctracheal tube of an intubated patient. The illumination may be with a light source providing a specific light wavelength, light dosage and a light dosage rate. The light wavelength may range from about 580 nm to about 680 nm. The light dosage may range from about 10 $J/cm^2$ to about 60 $J/cm^2$. The light dosage rate may range from about 50 $mw/cm^2$ to about 150 $mw/cm^2$. A similar process may be utilized for eradicating organisms upon an intravascular catheter or other medical device or prosthesis.

The reduction or elimination of airborne contaminants is desirable, if not essential, in some environments. The increasing threat of the use of biological weapons requires systems for the rapid and complete broad spectrum eradication of pathogens. Although many different gram positive and gram negative bacterial or viral pathogens may be employed as biological weapons, the present threats include anthrax, tularemia, plague and small pox. The reduction of airborne pathogens in commercial HVAC systems similarly requires rapid and complete broad spectrum eradication of these pathogens.

One embodiment of the invention disclosed herein outlines an apparatus for eradicating biological pathogens using a photosensitizer and benzalkonium chloride solution, a light source, a method for commingling the pathogens with the photosensitizer/benzalkonium chloride solution, and light exposure of the pathogen/photosensitizer/benzalkonium chloride mixture at sufficient energy levels at a predetermined wavelength. The photosensitizer may be selected from among a group of photosensitive materials or solutions. The light source may be an array of vertical cavity surface-emitting lasers (VCSELs), LED's, laser diodes, or one or more incandescent bulb(s).

Figure 6:
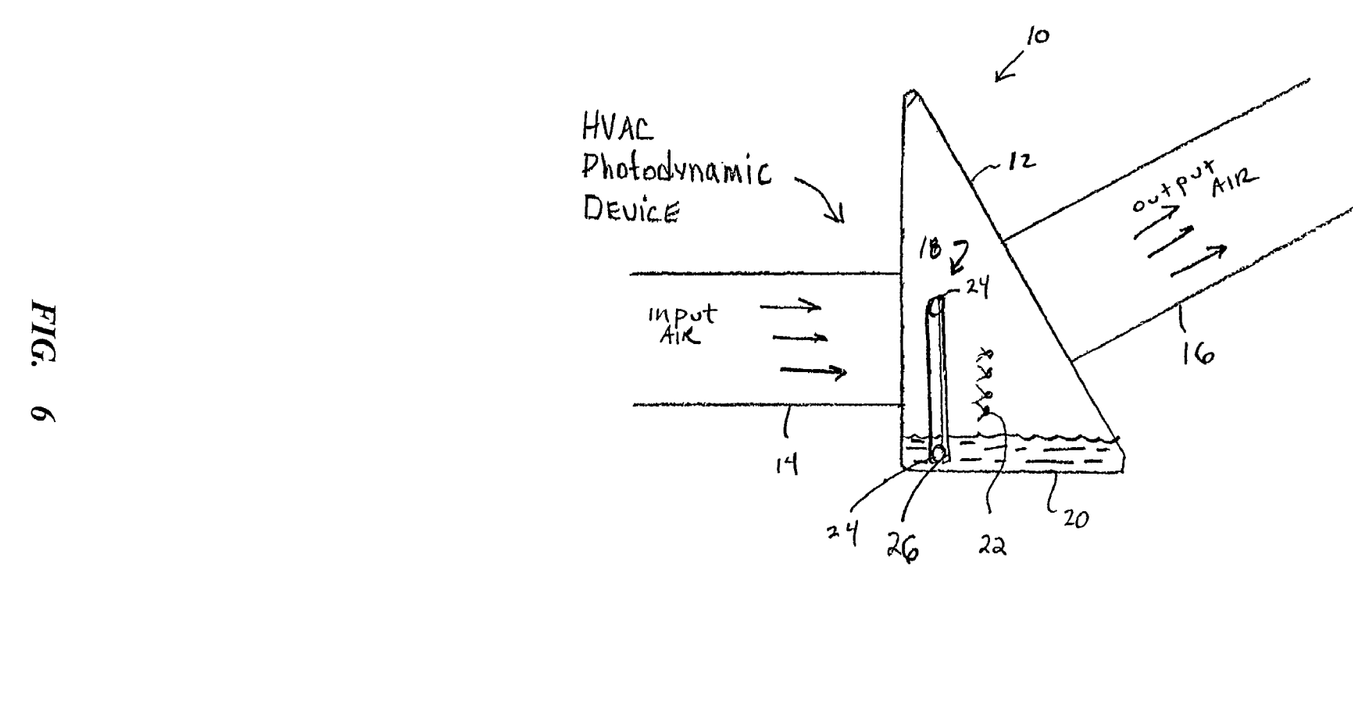

Referring now to FIG. 6, an air filtration device 10 according to the present invention is illustrated. The device 10 includes an enclosure structure 12 for housing the internal components of the filter 10 and for facilitating transportability of the device 10. The enclosure 12 illustrated may be sized for a building structure and may be placed in-line within the heating-air conditioning-ventilation (HVAC) system of the structure. Airflow through the enclosure 12 enters through an air intake 14 and exits through an air outlet 16. A driven fan or other air motive means (not shown) may be placed in any suitable location within the HVAC system. In some portable applications a fan may be placed within the enclosure of the filter device and be battery operated.

Within the enclosure 12 of the device 10 is a filter structure 18, a photosensitizer/benzalkonium chloride solution 20, and a light source 22 such as a VCSEL array. The filter structure 18 may be a flexible roll structure and may be maintained between rotating rollers 24 which impart a rotating motion to the roll 18. The lower end 26 of the roll structure 18 may be received into the photosensitizer/benzalkonium chloride solution 20 which bathes that portion of the filter structure 18. A variety of alternative filter structures 18 may be practicable, including but not limited to stationary filter media and other rotating or moving filter structures. The filter 18 is positioned to entrap incoming bacteria, fungi, or virus elements within its structure. The entrapped elements are then passed through the photosensitizer/benzalkonium chloride bath 20 as the filter 18 rotates about the rollers 24. The entrapped elements, then partially or completely enveloped with the photosensitizer/benzalkonium chloride solution 20 are subjected to illumination from the light source 22 to neutralize the elements.

Filter structures other than the flexible roll structure 18 may be used. For example, a generally flat disc-like filter may be rotated about its axis in a photosensitizer/benzalkonium chloride solution 20 or even a stationary filter (with solution 20 being applied upon) may be practicable. The photosensitizer/benzalkonium chloride solution 20 may be sprayed or otherwise applied to the surface of the filter structure 18 in a variety of known manners which are readily appreciated by those skilled in the art. The filter structure 18 may be replaceable or may be sealed within a disposable enclosure. Sizing of the entire filter 10 can result in the application of the filter technology in a variety of environments, such as building structures, vehicle environments, portable structures, or even in human mask form.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A method of photodynamic disruption of cellular organisms comprising:
- applying a surface acting agent containing benzalkonium chloride at a concentration of between 0.001% to 1.0% to a cell membrane of a cellular organism, said surface acting agent disorienting a cell membrane so that said cell membrane no longer functions as an effective osmotic barrier;
- passing a photosensitive material through the disoriented membrane and into the cell interior; and
- applying light to the cellular organism to cause a cellular disruption of the cellular organism.

2. The method of cellular organism disruption of claim 1 wherein the surface acting agent and the photosensitive material are provided in a combined solution.

3. The method of cellular organism disruption of claim 2 wherein the combined solution is provided in proximity to the cellular organism via a topical application.

4. The method of cellular organism disruption of claim 1 wherein the step of applying the surface acting agent and the step of passing the photosensitive material is performed on cellular organisms located on a surface of a medical prosthesis.

5. The method of cellular organism disruption of claim 1 wherein the photosensitive material is monomeric, dimeric, or polymeric.

6. The method of cellular organism disruption of claim 1 wherein the cellular organism is associated with an air filtration/decontamination process.

7. The method of cellular organism disruption of claim 1 wherein the cellular organism is a microbe, a spore, a fungus, or a cancer cell.

8. The method of cellular organism disruption of claim 1 wherein the surface acting agent contains benzalkonium chloride provided in a concentration range of between 0.005% to 0.05%.

9. The method of cellular organism disruption of claim 1 wherein the step of applying the surface acting agent precedes the step of passing the photosensitive material by between 1 to 30 minutes.

10. The method of cellular organism disruption of claim 1 wherein the step of applying light to the cellular organism occurs for a period of between 5 seconds to 1 hour and results in cellular organism death.

11. The method of cellular organism disruption of claim 1 wherein the step of applying a light includes a light wavelength ranging from 450 nm to 780 nm and a light dosage ranging from 10 $J/cm^2$ to 100 $J/cm^2$ and a light dosage rate ranging from 50 $mw/cm^2$ to 250 $mw/cm^2$.

12. The method of cellular organism disruption of claim 1 wherein the step of applying the surface acting agent includes providing more than one of a plurality of different surface acting agents.

13. The method of cellular organism disruption of claim 12 wherein the step of passing the photosensitive material includes providing more than one of a plurality of different photosensitive materials.

14. A method of photodynamic disruption of organisms comprising:
topically applying a surface acting agent containing benzalkonium chloride at a concentration of between 0.001% to 1.0% to a cell site with an organism, said surface acting agent disorienting a membrane of the organism so that said membrane no longer functions as an effective osmotic barrier;
passing a photosensitive material in association with the organism, said photosensitive material being accumulated within the membrane of the organism; and
applying light to the organism to cause a disruption of the organism.

15. The method of organism disruption of claim 14 wherein the surface acting agent and the photosensitive material are in a combined solution.

16. The method of organism disruption of claim 14 wherein the step of applying the surface acting agent and the step of passing the photosensitive material occurs on a surface of a medical prosthesis.

17. The method of organism disruption of claim 14 wherein the organism is associated with an air filtration/decontamination device.

18. The method of organism disruption of claim 14 wherein the photosensitizing agent is monomeric, dimeric, or polymeric.

19. The method of organism disruption of claim 14 wherein the benzalkonium chloride is provided in a concentration range of between 0.005% to 0.5%.

20. The method of organism disruption of claim 14 wherein the step of applying light results in organism destruction.

21. The method of organism disruption of claim 14 wherein the step of applying light occurs for a period of between 5 seconds to 1 hour and results in organism death.

22. The method of organism disruption of claim 21 wherein the step of applying light occurs for a period of between 2 to 20 minutes.

23. The method of acellular disruption of claim 14 wherein the step of applying the surface acting agent precedes the step of providing the photosensitive material by between 1 to 30 minutes.

24. The method of organism disruption of claim 14 wherein the step of applying the surface acting agent includes applying more than one of a plurality of different surface acting agents.

25. The method of organism disruption of claim 14 wherein the step of passing the photosensitive material includes passing more than one of a plurality of different photosensitive materials.

26. The method of organism disruption of claim 14 wherein the step of applying a light includes a light wavelength ranging from 450 nm to 780 nm and a light dosage ranging from 10 $J/cm^2$ to 100 $J/cm^2$ and a light dosage rate ranging from 50 $mw/cm^2$ to 250 $mw/cm^2$.

27. The method of organism disruption of claim 14 wherein the organism is from a group containing: a virus, a spore, and a plasmid.

28. A method of photodynamic disruption of cells comprising the steps of:
identifying an area of cell activity;
applying a concentration including a combination of a benzalkonium chloride compound at a concentration of between 0.001% to 1.0% and a photosensitive material to the area of cell activity, said benzalkonium chloride compound disorienting a cell membrane so that said membrane no longer functions as an effective osmotic barrier, and so that said photosensitive material is able to pass through the disoriented cell membrane; and
exposing the area of cell activity to light having a light wavelength, a light dosage and a light dosage rate to cause photodynamic cellular disruption.

29. The method of photodynamic disruption of cells of claim 28 wherein the step of identifying an area of cell activity includes an examination and identification of a cell site on a living body, and the step of applying the concentration includes an application of the concentration to the cell site of the living body.

30. The method of photodynamic disruption of cells of claim 28 wherein the step of identifying an area of cell activity includes identifying a medical prosthesis or device for sterilization procedure, and the step of providing the concentration includes an application of the concentration to a cell site of the prosthesis.

31. The method of photodynamic disruption of cells of claim 28 wherein the step of identifying an area of cell activity includes identifying an air filtration/decontamination device, and the step of providing the concentration includes an application of the concentration to a cell site within the device.

32. A method of photodynamic eradication of organisms within a biofilm of a medical prosthesis, said method comprising the steps of:
applying a photosensitive material and a surfactant to a surface of the prosthesis supporting a biofilm;
allowing the surfactant to disrupt membranes of the organisms within the biofilm;

waiting a period of time until the photosensitive material accumulates within the organisms;

providing a source of light illumination having predetermined light characteristics; and illuminating the organisms within the biofilm layer with the light source to achieve a photodynamic eradication of organisms within the biofilm layer.

33. The method of claim 32 wherein the surfactant is benzalkonium chloride provided in at a concentration of between 0.001% to 1.0%.

34. The method of claim 33 wherein the step of applying the photosensitive material and the surfactant is via an impregnation of compounds upon a surface of the prosthesis.

35. The method of claim 33 wherein the step of illuminating the biofilm layer is achieved by an internal illumination of the prosthesis.

36. The method of claim 33 wherein the step of illuminating the biofilm layer is achieved by an external light source illuminating the biofilm layer.

37. A method of photodynamic eradication of organisms within a biofilm layer of an endotracheal tube, said method comprising the steps of providing a photosensitive material and a surfactant to a surface of the endotracheal tube supporting a biofilm layer;

accumulating photosensitive material within the organisms comprising the biofilm;

allowing the surfactant to disrupt membranes of the organisms within the biofilm;

waiting a period of time until the photosensitive material accumulates within organisms;

providing a source of light illumination having predetermined light characteristics; and illuminating the biofilm layer of the endotracheal tube with the light source to achieve a photodynamic eradication of organisms within the biofilm layer.

38. The method of claim 37 wherein the surfactant is benzalkonium chloride provided at a concentration of between 0.001% to 1.0%.

39. The method of claim 37 wherein the step of providing the photosensitive material and the surfactant is via an impregnation of compounds upon a surface of the endotracheal tube.

40. The method of claim 37 wherein the step of illuminating the biofilm layer is achieved by an internal illumination of the endotracheal tube.

41. A method of photodynamic eradication of organisms within a biofilm layer of an intravascular catheter, said method comprising the steps of:

providing a photosensitive material and a surfactant to a surface of the intravascular catheter supporting a biofilm layer;

accumulating photosensitive material within organisms comprising the biofilm;

allowing the surfactant to disrupt membranes of organisms within the biofilm;

waiting a period of time until the photosensitive material accumulates within the membranes of organisms within the biofilm;

providing a source of light illumination having predetermined light characteristics; and illuminating the biofilm layer of the intravascular catheter with the light source to achieve a photodynamic eradication of organisms within the biofilm layer.

42. The method of claim 41 wherein the surfactant is benzalkonium chloride provided at a concentration of between 0.001% to 1.0%.

43. The method of claim 41 wherein the step of providing the photosensitive material and the surfactant is via an impregnation of compounds upon a surface of the intravascular catheter.

44. The method of claim 41 wherein the step of illuminating the biofilm layer is achieved by an internal illumination of the intravascular catheter.

* * * * *